United States Patent [19]
Takayanagi et al.

[11] Patent Number: 5,618,829
[45] Date of Patent: Apr. 8, 1997

[54] TYROSINE KINASE INHIBITORS AND BENZOYLACRYLAMIDE DERIVATIVES

[75] Inventors: Hisao Takayanagi, Machida; Yasunori Kitano, Yokohama; Tamaki Yano, Itabashi-ku; Hiroe Umeki, Yokohama; Hiroto Hara, Machida, all of Japan

[73] Assignee: Mitsubishi Chemical Corporation, Tokyo, Japan

[21] Appl. No.: 186,130

[22] Filed: Jan. 25, 1994

[30] Foreign Application Priority Data

Jan. 28, 1993 [JP] Japan .................................. 5-012618

[51] Int. Cl.$^6$ ..................... A01N 43/40; A61K 31/44; C07D 213/60; C07D 213/75
[52] U.S. Cl. ..................... 514/332; 546/304; 546/329; 546/340; 546/344; 546/346
[58] Field of Search ..................... 546/265, 304, 546/329, 340, 344, 346; 514/332

[56] References Cited

PUBLICATIONS

Caplus 1991:101537 (Mongelli et al, EP 388948 Sep. 26, 1990).

*Primary Examiner*—Shean C. Wu
*Attorney, Agent, or Firm*—Wenderoth, Lind & Ponack

[57] ABSTRACT

A pharmaceutical composition which comprises a pharmaceutically effective amount of a compound of the formula

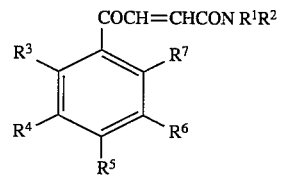

wherein $R^1$ represents a hydrogen atom, $R^2$ represents —$(CH_2)_m$-A wherein m is an integer of 0 to 3, and A represents pyridyl which is unsubstituted or is substituted by $C_1$–$C_3$ alkyl said alkyl being unsubstituted or substituted by phenyl, and $R^3$, $R^4$, $R^5$, $R^6$ and $R^7$ each independently represent a hydrogen atom, a halogen atom, $C_1$–$C_5$ alkyl which is unsubstituted or is substituted with a halogen atom or —$OR^{13}$ wherein $R^{13}$ represents a hydrogen atom or $C_1$–$C_5$ alkyl which is unsubstituted or is substituted with a halogen atom or phenyl, or when their adjacent substituents are taken together, they represent $C_1$–$C_3$ oxyalkylene having one or two oxygen atoms;
or a pharmaceutically acceptable salt thereof, and
a pharmaceutically acceptable carrier therefor.

5 Claims, No Drawings

TYROSINE KINASE INHIBITORS AND BENZOYLACRYLAMIDE DERIVATIVES

The present invention relates to novel tyrosine kinase inhibitors. In particular, it relates to benzoylacrylamide derivatives having tyrosine-specific protein kinase (referred to as "tyrosine kinase" hereinafter) inhibitory activity and pharmaceutically acceptable salts thereof, and a pharmaceutical composition containing said derivative as an essential component.

In chemotherapy for cancer, a lot of therapeutic agents have been put into practical use. However, most of them are not sufficiently effective in their therapeutic action. In addition, growth inhibiting action of them is not limited to cancer cells, the and therefore, they often cause serious side-effects, which make them unsatisfactory therapeutic agents.

It is well known that tyrosine kinase plays an important role in intercellular signal transduction and cell differentiation or growth. Accordingly, failure of control of tyrosine kinase activity in cells disorders intercellular signal transduction and causes abnormal cell differentiation/growth, which is considered to be directly responsible for the development of various diseases. In particular, it is known that tyrosine kinase is significantly associated with disorderly overgrowth of cancer cells. In fact, overexpression of tyrosine kinase is epidemiologically observed in various carcinomas.

On the basis of this finding, it has been proposed that an agent specifically inhibiting tyrosine kinase activity would be an anti-cancer agent having minor side-effects and exerting its therapeutic effect through novel mechanisms. Examples of such agent are Erbstatin, Lavendustin, Herbimycin A, and Genistein which are all derived from microorganisms. Additional example are synthetic compounds such as benzylidenemalonitrile (Japanese Patent Publication Kokai No. 138238/1990; Journal of Medical Chemistry, 32 p2344, 1989; ibid 34 p1896, 1991), α-cyanosuccinamide derivative (Japanese Patent Publication Kokai No. 222153/1988) 3,5-diisopropyl-4-hydroxystyrene derivative (Japanese Patent Publication Kokai No. 39522/1987), 3-5-di-t-butyl-4-hydroxystyrene derivative (Japanese Patent Publication Kokai No. 39523/1987), and Erbstatin analogue (Japanese Patent Publication Kokai NO.277347/1987).

Tyrosine kinase inhibiters previously known possess too moderate inhibitory activity to be used as an anti-cancer agent. Accordingly, the purpose of the present invention is to provide a family of novel compounds useful for suppressing the growth of cancer cells, which compounds are easily available, exhibit specific and intensive activity in inhibiting tyrosine kinase of the growth factor receptor, and show negligible side-effects compared with previously known anti-cancer agents.

The inventors of the present invention have devoted themselves to a study for developing the above-noted compounds, and have found that a new class of benzoylacrylamide derivatives have an unprecedented intensive activity in inhibiting tyrosin kinase and have a cancer cell growth inhibitory activity. The present invention has been accomplished on the basis of such findings.

One aspect of the present invention is to provide a tyrosine kinase inhibitor wich comprises as an essential ingredient a benzoylacrylamide derivative represented by formula (I):

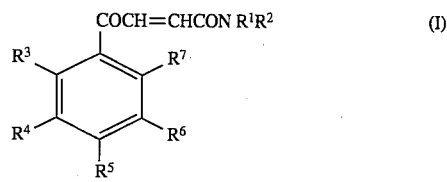

wherein $R^1$ and $R^2$ each independently represent a hydrogen atom, $C_1$~$C_5$ alkyl, $C_3$~$C_8$ cycloalkyl optionally intervened by —$NR^8$— ($R^8$ represents phenyl or $C_1$~$C_5$ alkyl which is unsubstituted or substituted with phenyl),

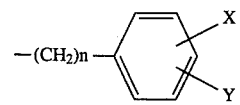

(n is an integer of 0 to 3 and X and Y each independently represent a hydrogen atom, a halogen atom, $C_1$~$C_5$ alkyl or $C_1$~$C_5$ alkoxy), —$(CH_2)$m-A (m is an integer of 0 to 3 and A represents an optionally substituted heterocycle), —$COR^9$ ($R^9$ represents $C_1$~$C_5$ alkyl which is unsubstituted or substituted with phenyl, phenyl which is unsubstituted or substituted with $C_1$~$C_5$ alkyl or a halogen atom, or $C_1$~$C_5$ alkoxy which is unsubstituted or substituted with phenyl) —$SO_2R^{10}$ ($R^{10}$ represents $C_1$~$C_5$ alkyl which is unsubstituted or substituted with phenyl or a halogen atom, or phenyl which is unsubstituted or substituted with $C_1$~$C_5$ alkyl), or —$OR^{11}$ ($R^{11}$ represents a hydrogen atom, or $C_1$~$C_5$ alkyl which is unsubstituted or substituted with phenyl); or when $R^1$ and $R^2$ are taken together, they represents $C_3$~$C_6$ alkylene optionally intervened by —O— or —$NR^{12}$ ($R^{12}$ represents a hydrogen atom, phenyl or $C_1$~$C_5$ alkyl); and $R^3$, $R^4$, $R^5$, $R^6$ and $R^7$ each independently represent a hydrogen atom, a halogen atom, $C_1$~$C_5$ alkyl which is unsubstituted or substituted with a halogen atom or —$OR^{13}$ ($R^{13}$ represents a hydrogen atom or $C_1$~$C_5$ alkyl which is unsubstituted or substituted with a halogen atom or phenyl); or when their adjacent substituents are taken together, they represent $C_1$~$C_3$ oxyalkylene having one or two oxygen atoms; or a pharmaceutically acceptable salt thereof.

The present invention is explained in detail below.

Tyrosin kinase inhibitors of the present invention are represented by formula (I):

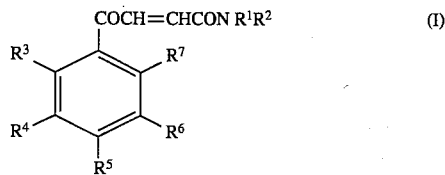

wherein $R^1$ and $R^2$ each independently represent a hydrogen atom, $C_1$~$C_5$ alkyl (e.g. methyl, propyl, pentyl or the like), $C_3$~$C_8$ cycloalkyl (e.g. cyclopropyl, cyclohexyl, cyclooctyl, or the like) optionally intervened by —$NR^8$— [$R^8$ represents phenyl or $C_1$~$C_5$ alkyl (e.g. methyl, propyl, pentyl or the like) which is unsubstituted or substituted with phenyl

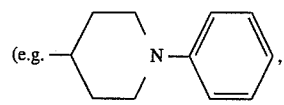

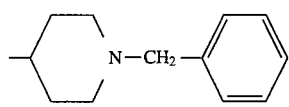

or the like)],

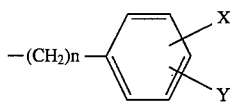

[n is an integer of 0 to 3 and X and Y each independently represent a hydrogen atom, a halogen atom (e.g. fluorine, chlorine, bromine, iodine or the like), $C_1$-$C_5$ alkyl (e.g. methyl, propyl, pentyl or the like), or $C_1$-$C_5$ alkoxy (e.g. methoxy, propoxy, pentyloxy or the like)], —(CH$_2$)m-A {m is an integer of 0 to 3 and A represents a heterocycle

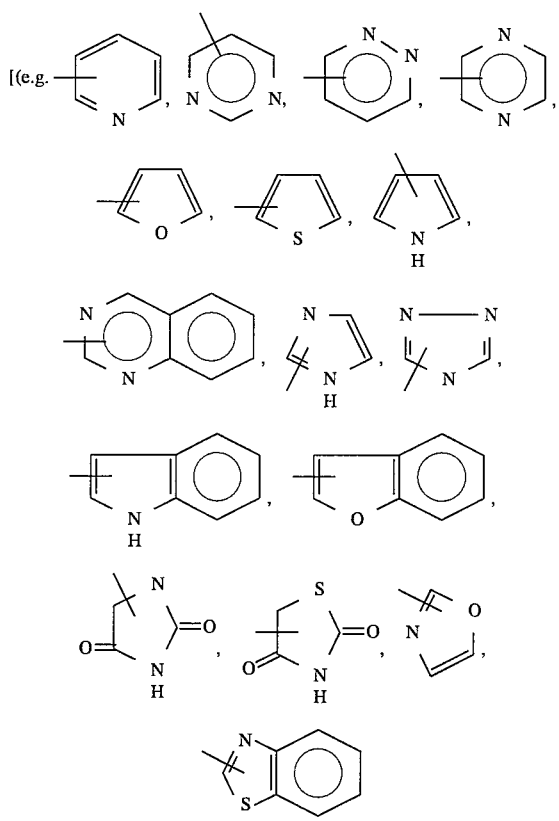

or the like) which has 1 to 4 heteroatoms selected from oxygen, sulfur and nitrogen atoms, and 5 to 10 atoms in total constituting the ring, preferably including aromatic heterocycle residues having one or more double bond] optionally substituted by $C_1$-$C_3$ alkyl (e.g. methyl, propyl or the like) which is unsubstituted or substituted with phenyl}, —COR$^9$ [R$^9$ represents $C_1$-$C_5$ alkyl (e.g. methyl, propyl, pentyl or the like) which is unsubstituted or substituted with phenyl, phenyl which is unsubstituted or substituted with $C_1$-$C_5$ alkyl (e.g. methyl, propyl, pentyl or the like) or a halogen atom (e.g. fluorine, chlorine, bromine, iodine atom or the like), or $C_1$-$C_5$ alkoxy (e.g. methoxy, propoxy, pentyloxy or the like) which is unsubstituted or substituted with phenyl], —SO$_2$R$^{10}$ [R$^{10}$ represents $C_1$-$C_5$ alkyl (e.g. methyl, propyl, pentyl or the like) which is unsubstituted or substituted with phenyl or a halogen atom (e.g. fluorine, chlorine, bromine, iodine atom or the like), or phenyl which is unsubstituted or substituted with $C_1$-$C_5$ alkyl (e.g. methyl, propyl, pentyl or the like)], or —OR$^{11}$ [R$^{11}$ represents a hydrogen atom, or $C_1$-$C_5$ alkyl (e.g. methyl, propyl, pentyl or the like) which is unsubstituted or substituted with phenyl)]; or when R$^1$ and R$^2$ are taken together, they represent $C_3$-$C_6$ alkylene optionally intervened by —O— or —NR$^{12}$ [R$^{12}$ represents a hydrogen atom, phenyl or $C_1$-$C_5$ alkyl (e.g. methyl, propyl, pentyl or the like)] (e.g. —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$OCH$_2$—, —CH$_2$CH$_2$NHCH$_2$CH$_2$—, —CH$_2$CH$_2$N(CH$_3$)CH$_2$CH$_2$—, —CH$_2$CH$_2$N(Ph)CH$_2$CH$_2$—, —CH$_2$CH$_2$N(C$_2$H$_5$)CH$_2$CH$_2$, —CH$_2$CH$_2$N(C$_3$H$_7$)CH$_2$CH$_2$— or the like) and R$^3$, R$^4$, R$^5$, R$^6$ and R$^7$ each independently represent a hydrogen atom, a halogen atom (e.g. fluorine, chlorine, bromine, iodine atom or the like), $C_1$-$C_5$ alkyl (e.g. methyl, propyl, pentyl or the like) which is unsubstituted or substituted with a halogen atom (e.g. fluorine, chlorine, bromine, iodine atom or the like), or —OR$^{13}$ [R$^{13}$ represents a hydrogen atom, or $C_1$-$C_5$ alkyl (e.g. methyl, propyl, pentyl or the like) which is unsubstituted or substituted with a halogen atom (e.g. fluorine, chlorine, bromine, iodine atom or the like) or phenyl]; or when their adjacent substituents are taken together, they represent $C_1$-$C_3$ oxyalkylene having one or two oxygen atoms (—OCH$_2$CH$_2$—, —CH$_2$OCH$_2$—, —CH$_2$CH$_2$O—, —OCH$_2$O— or the like); or pharmaceutically acceptable salt thereof.

Preferable inhibitors of the present invention are those represented by the above-noted formula (I) (1) wherein R$^1$ is hydrogen; R$^2$ is hydrogen, $C_3$-$C_8$ cycloalkyl,

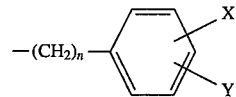

(X and Y are independently hydrogen, halogen or $C_1$-$C_3$ alkyl and n is as defined above), —(CH$_2$)$_m$-A (A is heterocycle optionally substituted with $C_1$-$C_3$ alkyl which is optionally substituted with phenyl and m is as defined above),

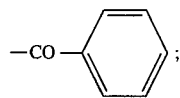

R$^3$, R$^6$ and R$^7$ are hydrogen; R$^4$ is hydrogen or —OR$^{13}$ (R$^{13}$ is hydrogen or $C_1$-$C_3$ alkyl and R$^5$ is —OR$^{13}$ (R$^{13}$ is hydrogen or $C_1$-$C_3$ alkyl); and R$^5$ is —OR$^{13}$ (R$^{13}$ is hydrogen or $C_1$-$C_3$ alkyl optionally substituted by phenyl or halogen), or (2) wherein R$^1$ and R$^2$ are taken together to form alkylene intervened by a group —O— or NR$^{12}$— (R$^{12}$ is phenyl or $C_1$-$C_3$ alkyl).

Preferable A in the definition of R$^2$ is furyl, pyrroly optionally substituted by methyl, pyridyl, N-benzylpiperazinyl or indolyl.

The present invention also provides the benzoylacrylamide derivatives of the formula (I) (3) wherein R$^1$ represents a hydrogen atom; R$^2$ represents $C_3$-$C_8$ cycloalky, —(CH$_2$)$_m$-A (m is an integer of 0–3, and A represents an optionally substituted heterocycle), or

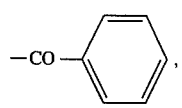

or when $R^1$ and $R^2$ are taken together, they represent $C_3$-$C_6$ alkylene optionally intervened with —O— or —$NR^{12}$ ($R^{12}$ represents a hydrogen atom, phenyl or $C_1$-$C_5$ alkyl); $R^3$, $R^4$, $R^5$, $R^6$, and $R^7$ each independently represent a hydrogen atom or —$OR^{13}$ ($R^{13}$ represents a hydrogen atom or $C_1$-$C_5$ alkyl which is unsubstituted or substituted with a halogen atom or phenyl), or a pharmaceutical acceptable salt thereof or (4) wherein $R^1$ represents a hydrogen atom; $R^2$ represents

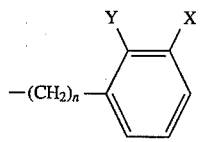

(n is an integer of 0–3, X represents a hydrogen atom, a chlorine atom or methyl; and Y represents a hydrogen atom or a chlorine atom, provided that one of X and Y must be hydrogen); $R^3$, $R^6$ and $R^7$ are hydrogen; $R^4$ represents a hydrogen atom or —$OR^{13}$ ($R^{13}$ represents a hydrogen atom or $C_1$-$C_3$ alkyl); $R^5$ represents —$OR^{13}$ ($R^{13}$ represents a hydrogen atom or $C_1$-$C_3$ alkyl which is unsubstituted or substituted by halogen or phenyl), or a pharmaceutically acceptable salt thereof.

Preferable compounds among the compounds of (3) those are of the formula (I) wherein A in the definition of $R^2$ is furyl, pyrrolyl whose nitorogen atom is unsubstituted or substituted by methyl, pyridyl, N-benzylpiperazinyl or indolyl, or of the formula (I) wherein $R^3$, $R^6$ and $R^3$ are hydrogen, and $R^4$ and $R^5$ are independently —$OR^{13}$ ($R^{13}$ is $C_1$-$C_3$ alkyl).

And preferable compounds among the compounds of (4) are those of the formula (I) wherein $R^2$ is

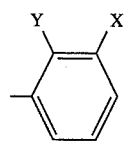

(X and Y are as defined above),

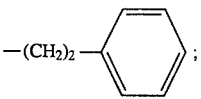

(X is hydrogen or chlorine), or

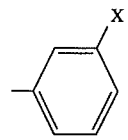

$R^4$ and $R^5$ are methoxy, or of the formula (I) wherein $R^2$ is

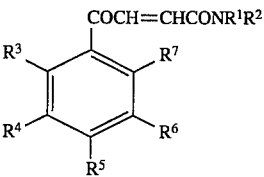

(X is hydrogen or chlorine); $R^4$ is hydorgen or —$OR^{13}$ ($R^{13}$ is hydrogen or methyl); and $R^5$ is —$OR^{13}$ ($R^{13}$ is hydrogen, methyl, difluoromethyl or benzyl).

The salts of the benzoylacrylamide derivatives of formula (I) include, for example, inorganic-acid salts such as carbonates, bicarbonates, hydrochlorides, sulfates and phosphates; or organic-acid salts such as formates, propionates, oxalates, fumarates, maleates, citrates, tartrates, benzoates, phthalates, methanesulfonates and 4-toluenesulfonates.

Preferable examples of the compounds of the present invention are shown below in Table 1 referring to the formula (I).

$$COCH=CHCONR^1R^2 \quad (I)$$

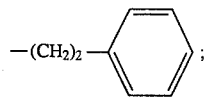

TABLE 1

| Compound No. | $R^1$ | $R^2$ | $R^3$ | $R^4$ | $R^5$ | $R^6$ | $R^7$ |
|---|---|---|---|---|---|---|---|
| 1 | —H | —H | —H | —H | —OMe | —H | —H |
| 2 | —H | —H | —H | —OMe | —OMe | —H | —H |
| 3 | —H | —H | —OMe | —H | —H | —OMe | —H |
| 4 | —H | —H | —H | —OH | —OH | —H | —H |
| 5 | —H | —H | —H | —OCH$_2$O— | | —H | —H |
| 6 | —H | —H | —H | —CH$_2$CH$_2$O— | | —H | —H |
| 7 | —H | —H | —H | —OMe | —OCHF$_2$ | —H | —H |
| 8 | —H | —H | —H | —OMe | —OH | —H | —H |
| 9 | —H | —H | —H | —OMe | —OCH$_2$Ph | —H | —H |
| 10 | —H | —H | —H | —Cl | —OH | —H | —H |
| 11 | —H | —H | —H | —Cl | —OH | —OH | —H |
| 12 | —H | —H | —H | -t.Bu | —OH | -t.Bu | —H |
| 13 | —H | -Me | —H | —H | —H | —H | —H |
| 14 | —H | -Me | —H | —H | —OMe | —H | —H |
| 15 | —H | -Me | —H | —OMe | —OMe | —H | —H |
| 16 | —H | -Me | —H | —OMe | —OCHF$_2$ | —H | —H |
| 17 | —H | -Me | —H | —OH | —OH | —H | —H |
| 18 | —H | —CH$_2$Ph | —H | —H | —OMe | —H | —H |

TABLE 1-continued

| Compound No. | R¹ | R² | R³ | R⁴ | R⁵ | R⁶ | R⁷ |
|---|---|---|---|---|---|---|---|
| 19 | —H | —CH₂Ph | —H | —OMe | —OMe | —H | —H |
| 20 | —H | —CH₂Ph | —H | —OH | —OH | —H | —H |
| 21 | —H | —CH₂Ph | —H | —CH₂OCH₂— | | —H | —H |
| 22 | —H | —CH₂Ph | —H | -t.Bu | —OH | -t.Bu | —H |
| 23 | -Me | -Me | —H | —H | —H | —H | —H |
| 24 | -Me | -Me | —H | —H | —OMe | —H | —H |
| 25 | -Me | -Me | —H | —OMe | —OMe | —H | —H |
| 26 | -Me | -Me | —H | —OH | —OH | —H | —H |
| 27 | -Me | -Me | —H | -t.Bu | —OH | -t.Bu | —H |
| 28 | -Et | -Et | —H | —H | —H | —H | —H |
| 29 | -Et | -Et | —H | —H | —OMe | —H | —H |
| 30 | -Et | -Et | —H | —OMe | —OMe | —H | —H |
| 31 | -Et | -Et | —H | —OMe | —OCHF₂ | —H | —H |
| 32 | -Et | -Et | —H | —OH | —OH | —H | —H |
| 33 | —(CH₂)₅— | | —H | —H | —H | —H | —H |
| 34 | —(CH₂)₅— | | —H | —H | —OMe | —H | —H |
| 35 | —(CH₂)₅— | | —H | —OMe | —OMe | —H | —H |
| 36 | —(CH₂)₅— | | —OMe | —H | —H | —OMe | —H |
| 37 | —(CH₂)₅— | | —H | -t.Bu | —OH | -t.Bu | —H |
| 38 | —(CH₂)₂O(CH₂)₂— | | —H | —H | —H | —H | —H |
| 39 | —(CH₂)₂O(CH₂)₂— | | —H | —H | —OMe | —H | —H |
| 40 | —(CH₂)₂O(CH₂)₂— | | —H | —OMe | —OMe | —H | —H |
| 41 | —(CH₂)₂O(CH₂)₂— | | —OMe | —H | —H | —OMe | —H |
| 42 | —(CH₂)₂O(CH₂)₂— | | —H | -t.Bu | —OH | -t.Bu | —H |
| 43 | —H | cyclohexyl | —H | —H | —H | —H | —H |
| 44 | —H | cyclohexyl | —H | —H | —OMe | —H | —H |
| 45 | —H | cyclohexyl | —H | —OMe | —OMe | —H | —H |
| 46 | —H | cyclohexyl | —OMe | —H | —H | —OMe | —H |
| 47 | —H | cyclohexyl | —H | -t.Bu | —OH | -t.Bu | —H |
| 48 | —H | -n.Pr | —H | —H | —H | —H | —H |
| 49 | —H | -n.Pr | —H | —H | —OMe | —H | —H |
| 50 | —H | -i.Pr | —H | —OMe | —OMe | —H | —H |
| 51 | —H | -i.Pr | —H | —OH | —OH | —H | —H |
| 52 | —H | -n.Bu | —H | —OMe | —OMe | —H | —H |
| 53 | —H | -n.Bu | —H | —OH | —OH | —H | —H |
| 54 | —H | -t.Bu | —H | —OMe | —OMe | —H | —H |
| 55 | —H | -t.Bu | —OMe | —H | —H | —OMe | —H |
| 56 | —H | -t.Bu | —H | —CH₂OCH₂— | | —H | —H |
| 57 | —H | -Ph | —H | —H | —H | —H | —H |
| 58 | —H | -Ph | —H | —H | —OMe | —H | —H |
| 59 | —H | -Ph | —H | —OMe | —OMe | —H | —H |
| 60 | —H | -Ph | —H | —OH | —OH | —H | —H |
| 61 | —H | -Ph | —H | —OMe | —OH | —H | —H |
| 62 | —H | -Ph | —H | —CH₂OCH₂— | | —H | —H |
| 63 | —H | -Ph | —H | -t.Bu | —OH | -t.Bu | —H |
| 64 | —H | -Ph | —H | —OMe | —OCHF₂ | —H | —H |
| 65 | —H | -Ph | —H | —H | —CF₃ | —H | —H |
| 66 | —H | -Ph | —H | —Cl | —OH | —H | —H |
| 67 | —H | -Ph | —H | —OMe | —OCH₂Ph | —H | —H |
| 68 | —H | -Ph | —OMe | —H | —H | —OMe | —H |
| 69 | —H | -Ph | —OH | —H | —H | —OH | —H |

TABLE 1-continued

| Compound No. | R¹ | R² | R³ | R⁴ | R⁵ | R⁶ | R⁷ |
|---|---|---|---|---|---|---|---|
| 70 | —H | 2-Cl-C₆H₄— | —H | —H | —H | —H | —H |
| 71 | —H | 2-Cl-C₆H₄— | —H | —OMe | —OMe | —H | —H |
| 72 | —H | 2-Cl-C₆H₄— | —H | —OH | —OH | —H | —H |
| 73 | —H | 3-Cl-C₆H₄— | —H | —H | —H | —H | —H |
| 74 | —H | 3-Cl-C₆H₄— | —H | —OMe | —OMe | —H | —H |
| 75 | —H | 3-Cl-C₆H₄— | —H | —OH | —OH | —H | —H |
| 76 | —H | 4-Cl-C₆H₄— | —H | —H | —H | —H | —H |
| 77 | —H | 4-Cl-C₆H₄— | —H | —OMe | —OMe | —H | —H |
| 78 | —H | 4-Cl-C₆H₄— | —H | —OH | —OH | —H | —H |
| 79 | —H | 2-Me-C₆H₄— | —H | —H | —H | —H | —H |
| 80 | —H | 2-Me-C₆H₄— | —H | —OMe | —OMe | —H | —H |

TABLE 1-continued
| Compound No. | R¹ | R² | R³ | R⁴ | R⁵ | R⁶ | R⁷ |
|---|---|---|---|---|---|---|---|
| 81 | —H | 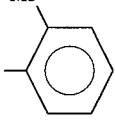 Me | —H | —OH | —OH | —H | —H |
| 82 | —H | 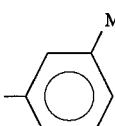 Me | —H | —H | —H | —H | —H |
| 83 | —H | 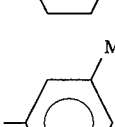 Me | H | —OMe | —OMe | —H | —H |
| 84 | —H | 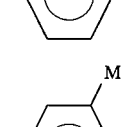 Me | —H | —OH | —OH | —H | —H |
| 85 | —H | 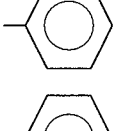 Me | —H | —H | —H | —H | —H |
| 86 | —H | 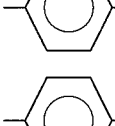 Me | —H | —OMe | —OMe | —H | —H |
| 87 | —H | 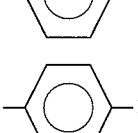 Me | —H | —OH | —OH | —H | —H |
| 88 | —H | 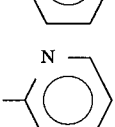 N | —H | —H | —H | —H | —H |
| 89 | —H | 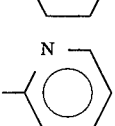 N | —H | —OMe | —OMe | —H | —H |
| 90 | —H | 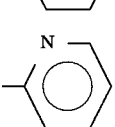 N | —H | —OH | —OH | —H | —H |
| 91 | —H | 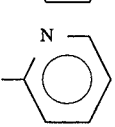 N | —H | -t.Bu | —OH | -t.Bu | —H |
| 92 | —H | 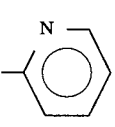 N | —H | —OCH₂O— | | —H | —H |

TABLE 1-continued

| Compound No. | R¹ | R² | R³ | R⁴ | R⁵ | R⁶ | R⁷ |
|---|---|---|---|---|---|---|---|
| 93 | —H | 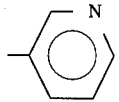 | —H | —H | —H | —H | —H |
| 94 | —H | 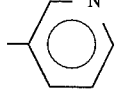 | —H | —H | —OMe | —H | —H |
| 95 | —H | 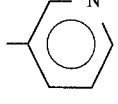 | —H | —OMe | —OMe | —H | —H |
| 96 | —H | 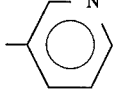 | —H | —OH | —OH | —H | —H |
| 97 | —H | 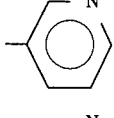 | —H | -t.Bu | —OH | -t.Bu | —H |
| 98 | —H | 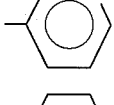 | —H | —OCH₂O— | | —H | —H |
| 99 | —H |  | —H | —H | —H | —H | —H |
| 100 | —H | 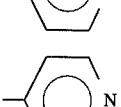 | —H | —H | —OMe | —H | —H |
| 101 | —H | 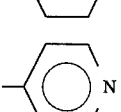 | —H | —OMe | —OMe | —H | —H |
| 102 | —H | 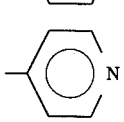 | —H | -t.Bu | —OH | -t.Bu | —H |
| 103 | —H | 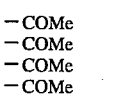 | —H | —OCH₂O— | | —H | —H |
| 104 | —H | —COMe | —H | —H | —H | —H | —H |
| 105 | —H | —COMe | —H | —H | —OMe | —H | —H |
| 106 | —H | —COMe | —H | —OMe | —OMe | —H | —H |
| 107 | —H | —COMe | —H | —OH | —OH | —H | —H |
| 108 | —H | —COPh | —H | —H | —H | —H | —H |
| 109 | —H | —COPh | —H | —H | —OMe | —H | —H |
| 110 | —H | —COPh | —H | —OMe | —OMe | —H | —H |
| 111 | —H | —COPh | —H | —OH | —OH | —H | —H |
| 112 | H | —COCH₂Ph | H | OMe | OMe | H | H |
| 113 | H | —COCH₂Ph | H | H | OMe | H | H |
| 114 | H | —COCH₂Ph | H | OH | OH | H | H |
| 115 | H | —CO₂Me | H | OMe | OMe | H | H |
| 116 | H | —CO₂Me | H | H | OMe | H | H |
| 117 | H | —CO₂Et | H | OMe | OMe | H | H |
| 118 | H | —CO₂Et | H | OH | OH | H | H |
| 119 | H | —CO₂CH₂Ph | H | OH | OH | H | H |

TABLE 1-continued

| Compound No. | R¹ | R² | R³ | R⁴ | R⁵ | R⁶ | R⁷ |
|---|---|---|---|---|---|---|---|
| 120 | H | —CO₂CH₂Ph | H | OMe | OMe | H | H |
| 121 | H | —CO₂CH₂Ph | H | H | Cl | H | H |
| 122 | H | —CO₂CH₂Ph | H | —OCH₂O— | | H | H |
| 123 | H | —CH₂CH₂Ph | H | —OCH₂O— | | H | H |
| 124 | H | —CH₂CH₂Ph | H | OMe | OMe | H | H |
| 125 | H | —CH₂CH₂Ph | H | OH | OH | H | H |
| 126 | H | —CH₂CH₂—(3-Cl-C₆H₄) | H | OH | OH | H | H |
| 127 | H | —CH₂CH₂—(3-Cl-C₆H₄) | H | OMe | OH | H | H |
| 128 | H | —CH₂CH₂—(3-Cl-C₆H₄) | H | OMe | OMe | H | H |
| 129 | H | —CH₂CH₂—(3-Cl-C₆H₄) | H | OMe | Cl | H | H |
| 130 | H | —CH₂CH₂—(4-Cl-C₆H₄) | H | OMe | OMe | H | H |
| 131 | H | —(CH₂)₃—C₆H₅ | H | OMe | OMe | H | H |
| 132 | H | —(CH₂)₃—C₆H₅ | H | OMe | OMe | H | H |
| 133 | H | cyclopropyl | H | OMe | OMe | H | H |
| 134 | H | cyclobutyl | H | OMe | OMe | H | H |
| 135 | H | cyclopentyl | H | OMe | OMe | H | H |
| 136 | H | cycloheptyl | H | OMe | OMe | H | H |
| 137 | H | cyclooctyl | H | OMe | OMe | H | H |

TABLE 1-continued

| Compound No. | R¹ | R² | R³ | R⁴ | R⁵ | R⁶ | R⁷ |
|---|---|---|---|---|---|---|---|
| 138 | H | 4-(N-phenylamino)piperidinyl | H | OMe | OMe | H | H |
| 139 | H | 4-(N-phenylamino)piperidinyl | H | OH | OH | H | H |
| 140 | H | 4-(N-phenylamino)piperidinyl | H | OMe | OH | H | H |
| 141 | H | 1-benzylpiperidin-4-yl | H | OMe | OMe | H | H |
| 142 | H | 1-benzylpiperidin-4-yl | H | —OCH₂O— | | H | H |
| 143 | H | 1-benzylpiperidin-4-yl | H | OH | OH | H | H |
| 144 | | —(CH₂)₂—N(Me)—(CH₂)₂— | H | OMe | OMe | H | H |
| 145 | | —(CH₂)₂—N(Me)—(CH₂)₂— | H | OMe | Cl | H | H |
| 146 | | —(CH₂)₂—N(Ph)—(CH₂)₂— | H | OMe | Cl | H | H |
| 147 | | —(CH₂)₂—N(Ph)—(CH₂)₂— | H | OMe | OMe | H | H |
| 148 | | —(CH₂)₂—N(H)—(CH₂)₂— | H | OMe | OMe | H | H |
| 149 | H | pyrimidin-2-yl | H | OMe | OMe | H | H |
| 150 | H | pyrimidin-2-yl | H | —CH₂OCH₂— | | H | H |
| 151 | H | pyrazin-2-yl | H | —CH₂OCH₂— | | H | H |
| 152 | H | pyrazin-2-yl | H | OMe | OMe | H | H |

TABLE 1-continued
| Compound No. | R¹ | R² | R³ | R⁴ | R⁵ | R⁶ | R⁷ |
|---|---|---|---|---|---|---|---|
| 153 | H | 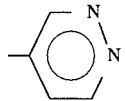 | H | OMe | OMe | H | H |
| 154 | H | 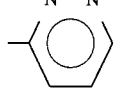 | H | OMe | OMe | H | H |
| 155 | H | 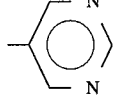 | H | OMe | OMe | H | H |
| 156 | H | 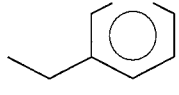 | H | OMe | OMe | H | H |
| 157 | H | 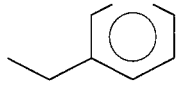 | H | —CH₂OCH— | | H | H |
| 158 | H | 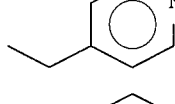 | H | —CH₂OCH— | | H | H |
| 159 | H | 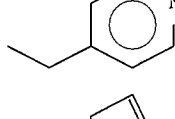 | H | OMe | OMe | H | H |
| 160 | H | 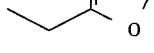 | H | OMe | OMe | H | H |
| 161 | H | 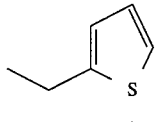 | H | OMe | OMe | H | H |
| 162 | H | 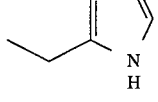 | H | OMe | OMe | H | H |
| 163 | H | 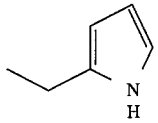 | H | OMe | OH | H | H |
| 164 | H | 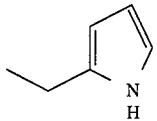 | H | OH | OH | H | H |

TABLE 1-continued

| Compound No. | $R^1$ | $R^2$ | $R^3$ | $R^4$ | $R^5$ | $R^6$ | $R^7$ |
|---|---|---|---|---|---|---|---|
| 165 | H | 3-propyl-indol-2-yl | H | OH | OH | H | H |
| 166 | H | 3-propyl-indol-2-yl | H | OMe | OMe | H | H |
| 167 | H | 2-propyl-indol-3-yl | H | OMe | OMe | H | H |
| 168 | H | thiazol-2-yl | H | OMe | OMe | H | H |
| 169 | H | benzothiazol-2-yl | H | OMe | OMe | H | H |
| 170 | H | —SO$_2$Me | H | OMe | OMe | H | H |
| 171 | H | —SO$_2$Ph | H | OMe | OMe | H | H |
| 172 | H | —SO$_2$CF$_3$ | H | OMe | OMe | H | H |
| 173 | H | —SO$_2$-(4-Me-C$_6$H$_4$) | H | OMe | OMe | H | H |
| 174 | H | —SO$_2$-(4-Me-C$_6$H$_4$) | H | OMe | OH | H | H |
| 175 | H | —SO$_2$CH$_2$Ph | H | OMe | OMe | H | H |
| 176 | H | —OH | H | OMe | OMe | H | H |
| 177 | H | —OH | H | OH | OH | H | H |
| 178 | H | —OH | H | H | Cl | H | H |
| 179 | H | —OCH$_2$Ph | H | OMe | OMe | H | H |
| 180 | H | —OCH$_2$Ph | H | OMe | OH | H | H |
| 181 | H | —OCH$_2$Ph | H | OMe | Cl | H | H |
| 182 | H | —OCH$_2$Ph | H | Cl | Cl | H | H |
| 183 | H | 3-propyl-pyridin-4-yl | H | Cl | Cl | H | H |
| 184 | H | 3-propyl-pyridin-4-yl | H | OMe | OMe | H | H |

TABLE 1-continued

| Compound No. | R¹ | R² | R³ | R⁴ | R⁵ | R⁶ | R⁷ |
|---|---|---|---|---|---|---|---|
| 185 | H | (n-butyl-pyridin-3-yl) | H | OMe | OMe | H | H |
| 186 | H | (n-propyl-1H-pyrrol-2-yl) | H | OMe | OMe | H | H |
| 187 | H | (ethyl-1H-imidazol-2-yl) | H | OMe | OMe | H | H |
| 188 | H | (n-propyl-thiazol-2-yl) | H | OMe | OMe | H | H |
| 189 | H | (n-butyl-1-methyl-pyrrol-2-yl) | H | OMe | OMe | H | H |

The compounds represented by the above formula (I) can be prepared by the route as shown below.

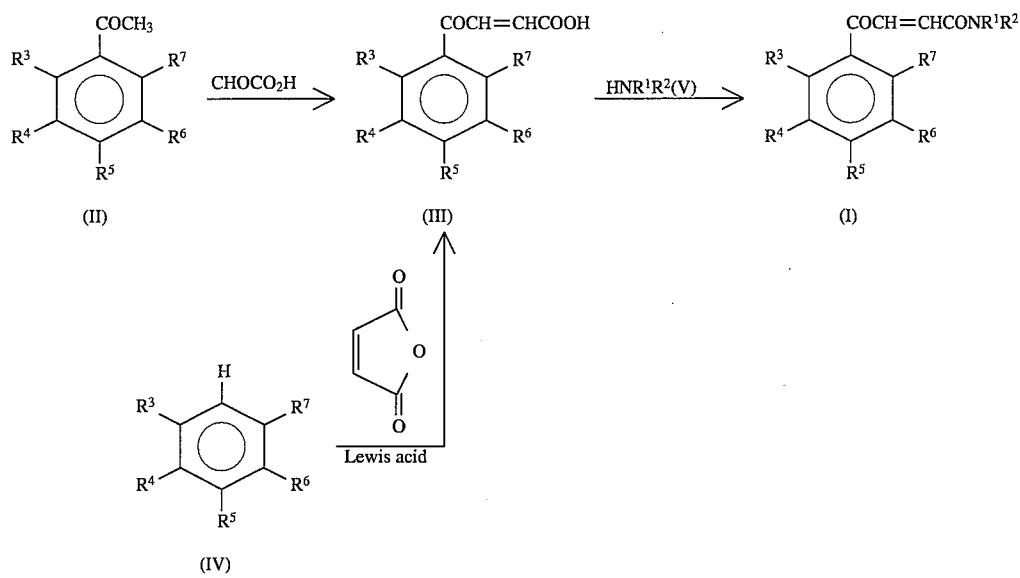

In the above formulae, $R^1$–$R^7$ are as defined in the above formula (I).

The benzoylacrylic acid represented by formula (III) can be prepared by, for example, reacting an acetophenone derivative represented by formula (II) with glyoxylic acid without a solvent or in a hydrocarbon solvent such as benzene or toluene, or an ether solvent such as tetrahydrofuran or dioxane, in the presence of a catalyst of an organic acid such as acetic acid or propionic acid (organic acids can serve both as a solvent and a catalyst), or an inorganic acid such as sulfuric acid or phosphoric acid or without catalyst at temperatures of –50° C. to 200° C. preferably 20° C. to 150° C., for 5 minutes to 48 hours, preferably 30 minutes to 5 hours. Compound (III) can be also prepared by, for example, reacting benzene or a benzene derivative represented by formula (IV) with maleic anhydride in the presence of a catalyst such as aluminiumchloride or tin (II) chloride (under a condition of the so-called Friedel-Crafts reaction).

The compounds of the present invention represented by formula (I) can be prepared by condensing compound (III) with an amine represented by formula (V): $R^1R^2NH$ wherein $R^1$ and $R^2$ are as defined in formula (I), without a solvent or in an appropriate solvent such as tetrahydrofuran, benzene or dimethylformamide in the presence or the absence of a condensing agent. Condensing agents include the above-mentioned acids and bases and further inorganic condensing agents such as phosphorus oxychloride and thionyl chloride, and organic condensing agents such as dicyclohexylcarbodiimide and carbonyldiimidazole.

The compounds represented by formula (I) can be also prepared by, for example, reacting compound (III) with thionyl chloride, phosphorus pentachloride or the like to form an acid halide or with ethyl formate, isobutyl formate or the like in the presence of an organic base such as triethylamine or pyridine to form an active mixed acid anhydride, and then reacting the resulting product with compound (V) in the presence of an organic base such as triethylamine or pyridine or an inorganic base such as sodium hydroxide, potassium hydroxide or sodium hydrogencarbonate.

The compounds represented by the formula (I) wherein $R^3$ to $R^7$ represent $—OR^{11}$ ($R^{11}$=a hydrogen atom) can be also prepared by reacting a compound represented by formula (I) wherein the corresponding $R^{11}$ represents $C_1 \sim C_5$ alkyl which is unsubstituted or substituted with a halogen atom or a phenyl with boron trichloride, trimethylsilyl iodide, anhydrous aluminum chloride-pyridine complex or the like in an appropriate solvent such as methylene chloride or acetonitrile (under so-called dealkylation condition).

The compounds represented by formula (I) wherein $R_1$ and $R^2$ represent $—COR^9$ or $—SO_2R^{10}$ can be prepared by reacting a compound represented by formula (I) wherein the corresponding $R^1$ and $R^2$ represents a halogen atom with an acid chloride or acid anhydride such as $ClCOR^9$, $(RCO)_2O$, $ClSO_2R^{10}$ or $(R^{10}SO_2)_2O$ in the presence of an organic base such as pyridine or triethylene in an appropriate solvent such as methylene chloride or tetrahydrofuran.

The compounds represented by formula (I) or salts thereof are useful as a tyrosine kinase inhibitor as described hereinafter and may be used as an anti-cancer agent, an immunosuppressor, a platelet aggregation inhibitor, an anti-arteriosclerosis agent, an anti-inflammatory agent, and the like.

A pharmaceutical composition containing a compound of the formula (I), which is useful as a tyrosine kinase inhibitor and an anti-cancer agent can be fromulated into various dosage forms for oral, enteral or parenteral administration. Specific formulations include tablets, capsules, fine granules, syrup, suppositories, ointments, injections and the like.

As carriers for preparing such composition in the form of pharmaceutical formulation, there are used pharmaceutical carriers suitable for oral, enteral or parenteral administration, such as organic or inorganic, and solid or liquid substances which are inactive. Specifically, the carriers include, for example, microcrystalline cellulose, gelatin, lactose, starch, magnesium stearate, talc, vegetable fat and oil, animal fat and oil, gum and polyalkylene glycol. The ratio of the compound (I) useful as a tyrosine kinase inhibitor or an anti-cancer agent to a carrier in a formulation can vary in the range of the ratio of 0.2 to 100% by weight.

The pharmaceutical composition of the invention useful as a tyrosine kinase inhibitor and anti-cancer agent may contain other substances effective as a tyrosine kinase inhibitor and anti-cancer agent. In this case, the compound of the invention may not be a major component of the composition.

The compositions of the invention in the form of a pharmaceutical formulation are generally administered in an amount by which desirable effects can be obtained with no side effect. Particular dosage of the formulation should be determined depending on physician's judgement, but it typically ranges from 10 mg to 10 g, and preferably 20 mg to 5 g, per day for an adult. The compound (I) of the present invention may be administered as an active ingredient in an amount of 1 mg to 5 g, and more preferably 3 mg to 1 g, per day for an adult.

The following detailed examples are presented by way of illustration of certain specific embodiments of the invention. The examples are representative only and should not be construed as limiting the invention in any respect.

Synthesis example 1

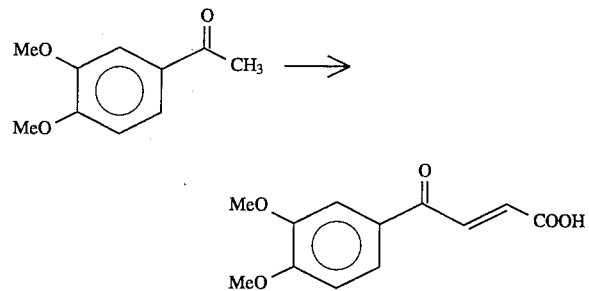

A solution of 3,4-dimethoxyacetophenone (10.00 g, 56 mmol) and glyoxylic acid monohydrate (5.11 g, 56 mmol) in acetic acid (11 ml) was heated under reflux for 20 hours. The reaction mixture was cooled and the precipitated solid was filtered off, washed with acetic acid, and dried with heating to give the above carboxylic acid (7.75 g, yield=59%).

m.p. 175°~177° C.

NMR (DMSO 250 MHz) δppm; 3.86 (s, 3H), 3.89 (s, 3H), 6.68 (d, 1H, J=15.4 Hz), 7.11 (d, 1H, J=8.5 Hz), 7.51 (d, 1H), 7.77 (dd, 1H, $J_1$=2.0 Hz, $J_2$=7.8 Hz), 7.94 (d, 1H, J=15.5 Hz).

EXAMPLE 1

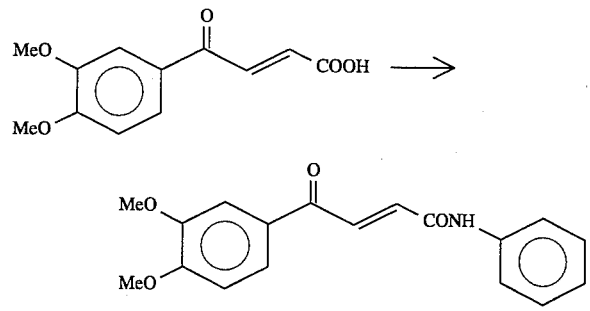

To an ice-cooling solution of the carboxylic acid obtained in Synthesis example 1 (3.00 g, 12.7 mmol), aniline (1.16 ml, 12.7 mmol) and triethylamine (2.34 ml, 15.3 mmol) in tetrahydrofuran (30 ml) was dropwise added phosphorus oxychloride (1.43 ml, 15.3 mmol). The reaction mixture was stirred overnight at room temperature, and the reaction was quenched by the addition of water. The resulting mixture was extracted twice with ethyl acetate, and the organic solvents were washed with saturated sodium hydrogen carbonate (aqueous) solution, 1N hydrochloric acid and brine, dried over anhydrous magnesium sulfate and filtered. The filtrate was concentrated in vacuo. The resulting residue was purified by recrystallization from hexane/ethyl acetate to give the above amide (1.85 g, yield=47%).

m.p. 186°~187° C.

NMR (DMSO 250 MHz) δppm; 3.86 (s, 3H), 3.89 (s, 3H), 7.11~7.15 (m, 2H), 7.17 (d, 1H, J=15.0 Hz), 7.37 (t, 2H), 7.55 (s, 1H), 7.61 (d, 2H, J=12 Hz), 7.81 (d, 1H, J=S.3 Hz), 7.97 (d, 1H, J=15.3 Hz), 10.60 (bs, 1H).

The compounds of the following Examples 2 to 10 were synthesized in a manner similar to that in Example 1.

EXAMPLE 2

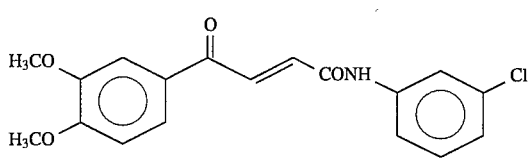

Yield 64%, m.p. 174°~175° C.

NMR (DMSO-d$_6$, 250 MHz) δppm; 3.87 (s, 3H), 3.97 (s, 3H), 6.93 (d, 1H, J=8.5 Hz), 7.26 (d, 1H, J=4.4 Hz), 7.21~7.30 (m, 1H), 7.43 (d, 1H, J=15.0 Hz), 7.54 (d, 1H, J=2.0 Hz), 7.75 (d, 1H, J=11.5 Hz), 7.81 (s, 1H), 7.84 (d, 1H, J=8.5 Hz), 8.16 (d, 1H, J=14.9 Hz), 9.21 (bs, 1H).

EXAMPLE 3

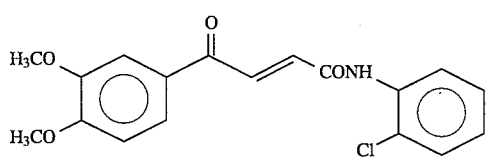

Yield 43%, m.p. 148°~149° C.

NMR (DMSO-d$_6$, 250 MHz) δppm; 3.86 (s, 3H), 3.88 (s, 3H), 7.14 (d, 1H, J=8.5 Hz), 7.20~7.90 (m, 1H), 7.38 (d, 1H, J=14.9 Hz), 7.36~7.42 (m, 1H), 7.54~7.57 (m, 2H), 7.78~7.95 (m, 2H), 7.98 (d, 1H, J=15 Hz), 10.21 (bs, 1H).

EXAMPLE 4

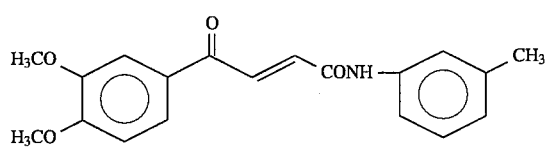

Yield 49%, m.p. 148°~151° C.

NMR (DMSO-d$_6$, 250 MHz) δppm; 3.34 (s, 3H), 3.86 (s, 3H), 3.88 (s, 3H), 6.93 (d, 1H, J=8.3 Hz), 7.12~7.18 (m, 1H), 7.15 (d, 1H, J=14.5 Hz), 7.20, 7.28 (m, 1H), 7.50~7.53 (m, 3H), 7.80 (d, 1H, J=8.3 Hz), 7.95 (d, 1H, J=15.0 Hz), 10.5 (bs, s).

EXAMPLE 5

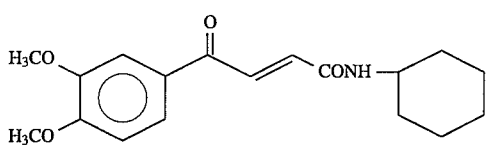

Yield 23%, m.p. 180°~182° C.

NMR (CDCl$_3$, 250 MHz) δppm; 1.19~1.29 (m, 3H), 1.34~1.44 (m, 2H), 1.61~1.77 (m, 3H), 1.98~2.01 (m, 2H), 3.90~3.94 (m, 1H), 3.96 (s, 3H), 3.97 (s, 3H), 5.97 (d, 1H, J=6.4 Hz), 6.93 (d, 1H, J=8.4 Hz ), 6.96 (d, 1H, J=14.9 Hz), 7.58 (d, 1H, J=1.9 Hz), 7.73 (dd, 1H, J=1.90 Hz, 8.3 Hz), 7.99 (d, 1H, J=14.9 Hz).

EXAMPLE 6

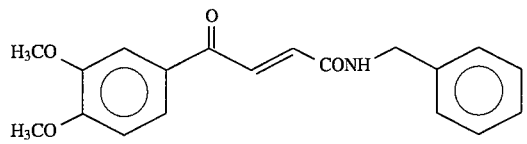

Yield 44%, m.p. 146°~149° C.

NMR (DMSO, 250 MHz) δppm; 3.85 (s, 3H), 3.87 (s, 3H), 4.43 (d, 2H, J=9.4 Hz), 7.05 (d, 1H, J=15.2 Hz), 7.12 (d, 1H, J=8.5 Hz), 7.30~7.35 (m, 5H), 7.51 (d, 1H, J=1.7 Hz), 7.77 (d, 1H, J=8.4 Hz), 7.87 (d, 1H, J=15.0 Hz), 9.10 (t, 1H).

EXAMPLE 7

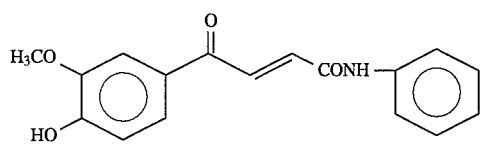

Yield 51%, m.p. 215°~218° C.

NMR (DMSO, 250 MHz ) δppm; 3.87 (s, 3H), 6.94 (d, 1H, J=8.5 Hz), 7.10~7.14 (m, 1H), 7.20 ( d, 1H, J=15 Hz), 7.33~7.40 (m, 2H), 7.75 (d, 1H, J=1.8 Hz), 7.66~7.74 (m, 3H), 7.94 (d, 1H, J=15 Hz), 10.29 (s, 1H), 10.58 (bs, 1H).

EXAMPLE 8

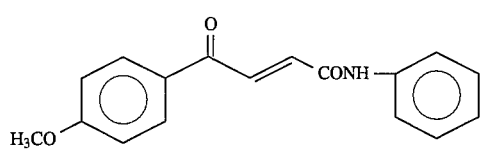

Yield 11%, m.p. 160°~162° C.

NMR (CDCl$_3$, 250 MHz) δppm; 3.90 (s, 3H), 6.99 (d, 2H, J=7.1 Hz), 7.09~7.20 (m, 1H), 7.23 (d, 1H, J=14.7 Hz), 7.34~7.41 (m, 2H), 7.67 (d, 2H, J=7.8 Hz), 8.06~8.65 (m, 2H), 8.12 (d, 1H, J=15.3 Hz).

EXAMPLE 9

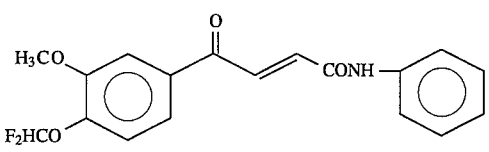

Yield 21%, m.p. 157°~158° C.

NMR (CDCl$_3$, 250 MHz) δppm; 3.90 (s, 3H), 6.67 (t, 1H, J=74.2 Hz), 7.10~7.26 (m, 2H), 7.29 (d, 1H, J=14.8 Hz), 7.33~7.40 (m, 2H), 7.62~7.69 (m, 4H), 8.08 (d, 1H, J=14.9 Hz), 8.33 (bs, 1H).

EXAMPLE 10

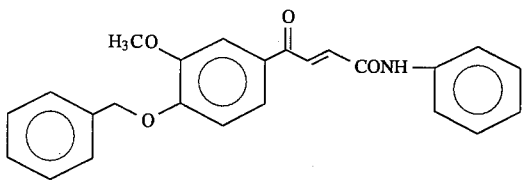

Yield 12%, m.p. 140° C. (dec.)

NMR (CDCl$_3$, 250 MHz) δppm; 3.90 (s, 3H), 5.25 (s, 2H), 6.95 (d, 1H, J=8.4 Hz), 7.16 (m, 1H), 7.26~7.43 (m, 8H), 7.60 (d, 1H, J=1.8 Hz ), 7.68 (d, 1H, J=8.2 Hz), 8.11 (d, 1H, J=14.8 Hz), 8.36 (bs, 1H).

EXAMPLE 11

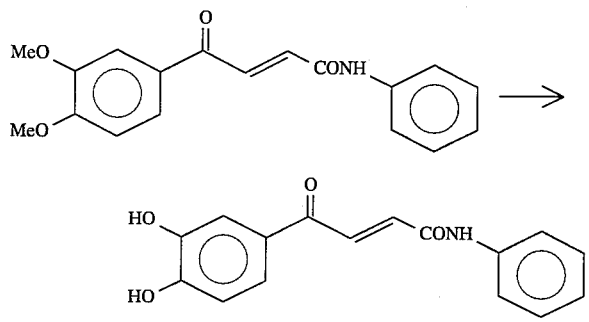

To a solution of the above carboxylic acid amide (380 mg, 1.22 mmol) obtained in Example 1 in dichloromethane (10 ml) is dropwise added and 1 mM solution of boron tribromide (5.60 ml) at −70° C. under a nitrogen atmosphere. The reaction mixture was gradually warmed to room temperature, stirred overnight at room temperature, and diluted with water under ice cooling. The resulting mixture was then stirred for one hour. The precipitate was filtered off and dried to give the above catechol (150 mg, yield=43%).

m.p. 230° C. (dec.)

NMR (DMSO, 250 MHz) δppm; 6.87 (d, 1H, J=8.3 Hz), 7.09~7.16 (m, 1H), 7.13 (d, 1H, J=15.5 Hz), 7.32~7.34 (m, 2H), 7.44 (s, 1H), 7.50 (d, 1H, J=8.3 Hz), 7.70 (d, 2H, J=7.8 Hz), 7.85 (d, 1H, J=15.0 Hz), 9.60 (bs, 1H), 10.18 (bs, 1H), 10.56 (bs, 1H).

EXAMPLE 12

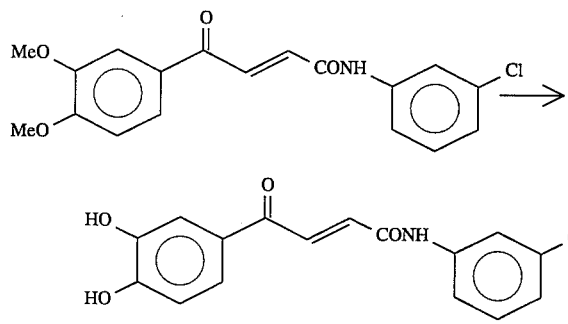

The above catechol was obtained with 32% yield in a manner similar to that in Example 11.

m.p. 250° C. (dec.)

NMR (DMSO, 250 MHz) δppm; 6.89 (d, 1H, J=8.3 Hz), 7.11 (d, 1H, J=15.0 Hz), 7.18 (d, 1H, J=9.8 Hz), 7.36~7.57 (m, 4H), 7.87 (d, 1H, J=15.3 Hz), 7.93 (s, 1H), 9.55 (bs, 1H), 10.15 (bs, 1H), 10.74 (bs, 1H).

EXAMPLE 13

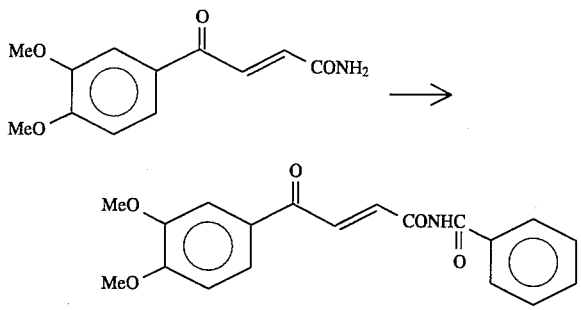

To a suspension of the above carboxylic acid (1.5 g, 6.36 mmol) obtained in Synthesis example 1 in carbon disulfide (10 ml) was added phosphorus pentachloride (1.6 g, 7.53 mmol). The resulting mixture was heated under reflux for 15 minutes. The reaction mixture was cooled and concentrated. A solution of the resulting residue in dichloromethane (5 ml) was poured into concentrated ammonia water (5 ml) under ice-cooling. The precipitated solid was filtered off, washed with 1N NaOH solution and water in this order and dried to afford the above amide (900 mg, yield=60%).

m.p. 188°~190° C.

NMR (DMSO, 250 MHz) δppm; 3.85 (s, 3H), 3.88 (s, 3H), 6.95 (d, 1H, J=15.3 Hz), 7.12 (d, 1H, J=9.3 Hz), 7.51 (s, 1H), 7.54 (s, 1H), 7.76 (d, 1H, J=8.7 Hz), 7.82 (d, 1H, J=15.5 Hz), 7.85 (s, 1H).

EXAMPLE 14

To a solution of the above carboxylic acid amide (250 mg, 1.06 mmol) obtained in Example 13 in pyridine (1 ml) in an ice bath was dropwise added benzoyl chloride (0.14 ml, 1.17 mmol). The ice bath was removed. The resulting mixture was stirred for 5 hours, and partitioned between water and ethyl acetate. Organic layer was separated, washed with 1N hydrochloric acid and saturated sodium bicarbonate aqueous solution in this order, dried over anhydrous magnesium sulfate and concentrated. The residue thus obtained was purified by column chromatography on SiO$_2$, eluting with hexane/ethyl acetate (2/1) to give the above benzoylamide (150 mg, yield=44%).

m.p. 170°~173° C.

NMR (CDCl$_3$, 250 MHz) δppm; 994 (d, 1H, J=8.4 Hz), 7.53~7.64 (m, 4H), 7.70 (dd, 1H, J$_1$=1.9 Hz, J$_2$=8.42 Hz), 7.91 (d, 2H, J=8.1 Hz), 8.90 (bs, 1H).

EXAMPLE 15

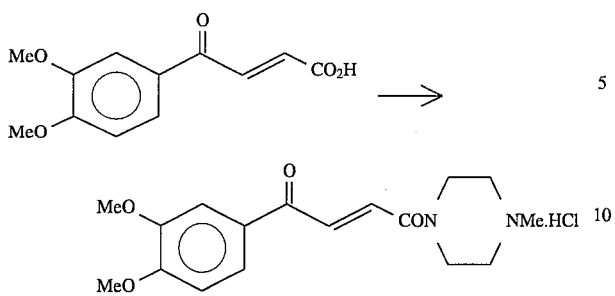

The starting material (carboxylic acid) (1.0 g, 3.21 mmol), triethylamine (0.39 g, 13.85 mmol) and N-methylpiperazine (0.32 g, 3.21 mmol) were dissolved in THF (20 ml). The solution was ice-cooled and phosphorus oxychloride (0.59 g, 3.85 mmol) was added. The resulting mixture was gradually warmed to room temperature and stirred overnight at room temperature. After completion of the reaction, water was added to the mixture under ice-cooling. The aqueous layer was washed with ether (30 ml×2), made basic with 2N NaOH solution, and extracted with ether (30 ml×2). The organic solvents was washed with water and brine, dried over anhydrous sodium sulfate and concentrated in vacuo. The residue was purified by column chromatography on silica gel eluting with chloroform/methanol (20:1). The product was dissolved in ethyl acetate, and hydrochloric acid/ethyl acetate is added thereto under ice-cooling. The precipitated crystals were filtered off and dried in vacuo to give the objective substance (150 mg, yield=12%).

$^1$H-NMR (DMSO-$d_6$, 250 MHz); 2.75 (s, 3H), 2.88~3.78 (m, 6H), 4.18~4.37 (m, 1H), 4.42~4.63 (m, 1H), 7.10 (d, 1H, J=8.5 Hz), 7.41 (d, 1H, J=15.2 Hz), 7.50 (d, 1H, J=1.7 Hz), 7.74 (dd, 1H, J=8.4, 1.7 Hz), 7.83 (d, 1H, J=15.1 Hz), 11.22 (brs, 1H).

IR (KBr) cm$^{-1}$ 3559, 3472, 2932, 2674, 2583, 2458, 1628, 1599, 1520, 1451, 1350, 1307, 1279, 1179, 1130, 1015, 970, 758, 571.

Pale yellow powder.
m.p. 205°~207° C.

EXAMPLE 16

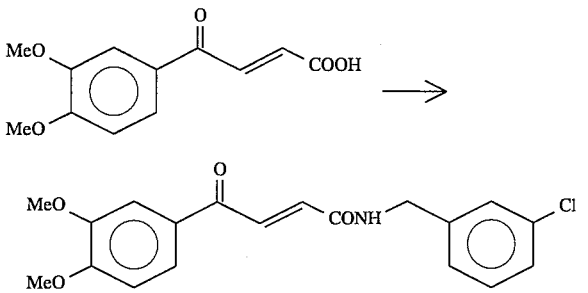

To an ice-cooled solution of the carboxylic acid (500 mg, 2.12 mmol) obtained in Synthesis example 1 and triethylamine (0.29 ml, 2.33 mmol) in tetrahydrofuran (20 ml) was dropwise added isobutyl chloroformate (0.33 ml, 2.54 mmol) under a nitrogen atmosphere. The reaction mixture was stirred in an ice-water bath for 30 minutes and 3-chlorobenzylamine (0.29 ml, 2.33 mmol) was dropwise added to the mixture in an ice-water bath. The resulting mixture was gradually warmed to room temperature and stirred for 2 hours. After completion of the reaction, water was added to the mixture. The resulting mixture was extracted twice with ethyl acetate. The extracts were washed with saturated sodium hydrogen carbonate solution, 1N hydrochloric acid and brine, dried over anhydrous sodium sulfate and filtered. Concentration of the solvents followed by recrystallization from hexane/ethyl acetate gave the desired amide (700 mg, yield=92%).

m.p. 150°~152° C., colorless needles.

NMR (CDCl$_3$, 250 MHz) δppm; 3.93 (s, 3H), 3.97 (s, 3H), 4.57 (d, 2H, J=6.0 Hz), 6.54 (brt, 1H, J=6.0 Hz), 6.92 (d, 1H, J=8.5 Hz), 7.04 (d, 1H, J=14.9 Hz), 7.18~7.31 (m, 4H), 7.55 (d, 1H, J=2.0 Hz), 7.69 (dd, 1H, J=8.5, 2.0 Hz), 8.05 (d, 1H, J=14.9 Hz).

IR (KBr) cm$^{-1}$; 3314, 3081, 2934, 1640, 1595, 1562, 1516, 1420, 1323, 1296, 1267, 1225, 1161, 1024, 966, 806.

The compounds of the following Examples 17~21 were synthesized in a manner similar to that in Example 16.

EXAMPLE 17

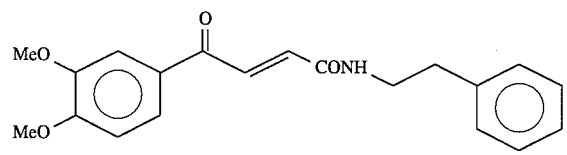

Yield 88%, m.p. 148°~150°C., colorless crystals.

NMR (CDCl$_3$, 250 MHz) δppm; 290 (t, 2H, J=6.9 Hz), 3.68 (q, 2H, J=6.9 Hz), 3.93 (s, 3H), 3.97 (s, 3H), 6.02 (brt, 1H, J=6.9 Hz), 6.89 (d, 1H, J=14.9 Hz), 6.92 (d, 1H, J=8.4 Hz), 7.19~7.37 (m, 5H), 7.57 (d, 1H, J=2.1 Hz), 7.71 (dd, 1H, J=8.4, 2.1 Hz), 7.99 (d, 1H, J=14.9 Hz).

IR (KBr) cm$^{-1}$; 3308, 2938, 1638, 1595, 1557, 1514, 1418, 1331, 1292, 1263, 1159, 1024, 970, 758, 700, 625.

EXAMPLE 18

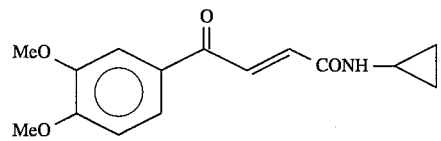

Yield 11%, m.p. 177°~179° C., yellow powder.

NMR (CDCl$_3$, 250 MHz) δppm; 0.60~0.67 (m, 2H), 0.84~0.95 (m, 2H), 2.87~2.97 (m, 1H), 3.96 (s, 3H), 3.97 (s, 3H), 6.57 (brs, 1H ), 6.93 (d, 1H, J=8.5 Hz), 6.98 ( d, 1H, J=14.9 Hz), 7.61 (d, 1H, J=2.1 Hz), 7.73 (dd, 1H, J=8.5, 2.1 Hz), 8.03 (d, 1H, J=14.9 Hz).

IR (KBr) cm$^{-1}$; 3270, 3011, 2045, 1634, 1578, 1520, 1464, 1437, 1412, 1348, 1317, 1277, 1233, 1200, 1173, 1132, 1017, 959, 916.

EXAMPLE 19

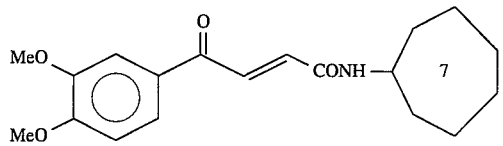

Yield 45%, m.p. 142°~143° C. colorless needle-shaped crystals.

NMR (CDCl$_3$, 250 MHz) δppm; 1.44~1.72 (m, 10H), 1.93~2.05 (m, 2H), 3.95 (s, 3H), 3.97 (s, 3H), 4.02~4.18 (m, 1H), 5.95 (brd, 1H, J=7.9 Hz), 6.92 (d, 1H, J=8.5 Hz), 6.93 (d, 1H, J=14.8 Hz), 7.58 (d, 1H, J=2.1 Hz), 7.72 (dd, 1H, J=8.5, 2.1 Hz), 7.98 (d, 1H, J=14.8 Hz).

IR (KBr) cm$^{-1}$; 3299, 2936, 2863, 1636, 1597, 1551, 1512, 1458, 1418, 1339, 1292, 1263, 1246, 1229, 1161, 1024, 985, 766.

EXAMPLE 20

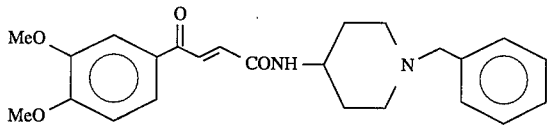

Yield 39%, m.p 168°~170° C. colorless powder.

NMR (CDCl$_3$, 250 MHz) δppm; 1.47~1.63 (m, 2H), 1.72 (brs, 1H), 1.90~2.05 (m, 2H), 2.11~2.22 (m, 2H), 2.79~2.88 (m, 2H), 3.52 (s, 2H), 3.95 (s, 3H), 3.97 (s, 3H), 5.92 (brd, 1H, J=8.0 Hz), 6.93 (d, 1H, J=8.2 Hz), 6.94 (d, 1H, J=15.0 Hz), 7.23~7.33 (m, 5H), 7.58 (d, 1H, J=2.0 Hz), 7.72 (dd, 1H, J=8.2, 2.0 Hz), 7.98 (d, 1H, J=15.0 Hz).

IR (KBr) cm$^{-1}$; 3291, 3077, 2936, 1636, 1582, 1553, 1517, 1462, 1420, 1341, 1292, 1269, 1227, 1161, 1020, 978.

EXAMPLE 21

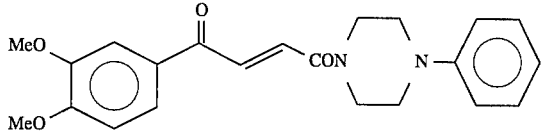

Yield 22%, m.p. 139°~140° C., yellow powder.

NMR (CDCl$_3$, 250 MHz) δppm; 3.19~3.28 (m, 4H), 3.78~3.86 (m, 2H), 3.87~3.94 (m, 2H), 3.97 (s, 3H), 3.98 (s, 3H), 6.89~6.97 (m, 4H), 7.26~7.34 (m, 2H), 7.53 (d, 1H, J=14.8 Hz), 7.60 (d, 1H, J=1.7 Hz), 7.73 (dd, 1H, J=8.3, 1.6 Hz), 8.01 (d, 1H, J=15.0 Hz).

IR (KBr) cm$^{-1}$; 2839, 1632, 1597, 1516, 1445, 1420, 1296, 1269, 1235, 1208, 1161, 1022, 959, 756.

EXAMPLE 22

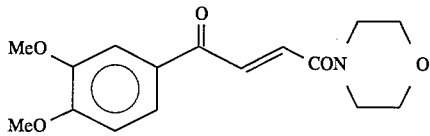

The crude product obtained by a method similar to that in Example 16 from the carboxylic acid (400 mg, 1.69 mmol) obtained in Synthesis example 1 and morpholine (160 mg, 1.86 mmol) was purified by column chromatography on silica gel, eluting with ethyl acetate to give the above carboxylic acid amide (120 mg, yield=23%).

Pale yellow oil.

NMR (CDCl$_3$, 250 MHz) δppm; 3.62~3.80 (m, 8H), 3.97 (s, 3H), 3.98 (s, 3H), 6.94 (d, 1H, J=8.5 Hz), 7.46 (d, 1H, J=15.0 Hz), 7.59 (d, 1H, J=2.0 Hz), 7.72 (dd, 1H, J=8.5, 2.0 Hz), 8.01 (d, 1H, J=15.0 Hz).

IR (neat) cm$^{-1}$; 2395, 2967, 2920, 2857, 2361, 2033, 1632, 1597, 1516, 1421, 1269, 1163, 1115, 1020, 972, 918, 756.

EXAMPLE 23

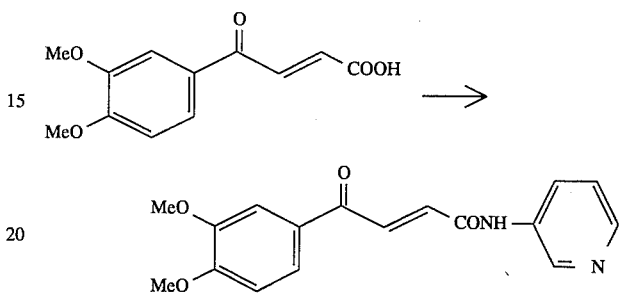

To a solution of the above carboxylic acid (0.366 g, 1.55 mmol) obtained by synthesis example 1 and triethylamine (0.32 ml, 2.32 mmol) in anhydrous tetrahydrofuran (20 ml) was dropwise added isobutyl chloroformate (0.23 ml, 1.86 mmol) at −5° C. to 0° C. under a nitrogen atmosphere. The resulting mixture was stirred for 5 minutes and a solution of 3-aminopyridine (0.16 g, 1.7 mmol) in anhydrous tetrahydrofuran (5 ml) was dropwise added. The resulting mixture was stirred for 15 minutes and the reaction was quenched by the addtion of ice pieces. The resulting mixture was extracted with dichloromethane. The exracts were washed with brine, dried over anhydrous Na$_2$SO$_4$ and filtered. The filtrate was concentrated in vacuo and the resulting crystals were washed with ether to give the above carboxylic acid amide (0.116 g, yield=25%).

m.p. 179°~180° C.

NMR (CDCl$_3$, 250 MHz) δppm; 3.92 (s, 3H), 3.99 (s, 3H), 6.96 (d, 1H, J=8.5 Hz), 7.29 (d, 1H, J=14.8 Hz), 7.34 (dd, 1H, J=8.4, 4.8 Hz), 7.59 (d, 1H, J=1.9 Hz), 7.76 (dd, 1H, J=8.4, 1.9 Hz), 8.17 (d, 1H, J=14.8 Hz), 8.34 (d, 1H, J=8.5 Hz), 8.41 (d, 1H, J=4.8 Hz), 8.68 (bs, 1H), 8.76 (bs, 1H).

IR (KBr) cm$^{-1}$; 3319, 1687, 1649, 1616, 1591, 1535, 1516, 1471, 1419, 1334, 1305, 1263, 1207, 1159, 1020, 964, 912, 887, 866, 804, 758, 707, 677, 828, 605, 565, 522, 478.

EXAMPLE 24

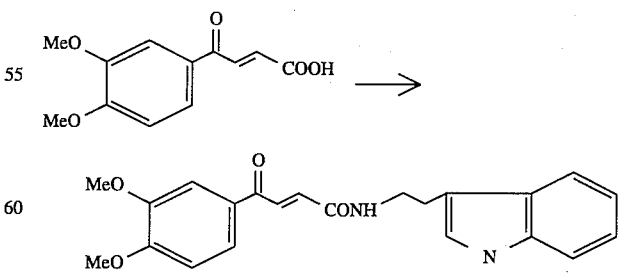

The above carboxylic acid amide was obtained in a manner similar to that in the above example. (Yield=88%).

m.p. 160°~161° C.

NMR (CDCl₃, 250 MHz) δppm; 3.06 (t, 2H, J=6.7 Hz), 3.76 (q, 1H, J=6.7 Hz), 3.93 and 3.96 (2s, 6H), 5.95~6.12 (m, 1H), 6.84 (d, 1H, J=14.8 Hz), 6.89 (d, 1H, J=8.4 Hz), 7.05 (d, 1H, J=2.0 Hz), 7.13 (dt, 1H), J=6.9, 1.2 Hz), 7.21 (dt, 1H, J=7.0, 1.2 Hz), 7.39 (d, 1H, J=7.8 Hz), 7.56 (d, 1H, J=1.9 Hz), 7.62 (d, 1H, J=7.8 Hz), 7.68 (dd, 1H, J=8.4, 1.9 Hz), 7.97 (d, 1H, J=14.8 Hz), 8.19 (bs, 1H).

IR (KBr) cm⁻¹: 3393, 3333, 2928, 1641, 1589, 1550, 1460, 1419, 1311, 1261, 1222, 1190, 1161, 1097, 1020, 964, 910, 866, 833, 763, 746, 692, 625, 599, 561, 426.

EXAMPLE 25

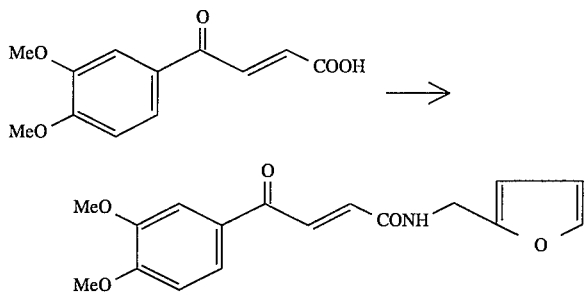

The above carboxylic acid amide was obtained in a manner similar to that in the above example. (Yield=75%).
m.p. 144.5°~147° C.

NMR (CDCl₃, 250 MHz) δppm; 3.39 (s, 3H), 3.97 (s, 3H), 4.59 (d, 2H, J=5.6 Hz), 6.28~6.34 (m, 2H), 6.64~6.79 (m, 1H), 6.92 (d, 1H, J=8.5 Hz), 7.04 (d, 1H, J=14.8 Hz), 3.35 (m, 1H), 7.57 (d, 1H, J=2 Hz), 7.70 (dd, 1H, J=8.45, 2 Hz), 8.03 (d, 1H, J=14.8 Hz).

IR (KBr) cm³¹ ¹; 3314, 3134, 3055, 3003, 2941, 2623, 2498, 1641, 1591, 1572, 1539, 1518, 1466, 1348, 1319, 1275, 1194, 1172, 1132, 1074, 1022, 976, 906, 850, 817, 783, 765, 690.

EXAMPLE 26

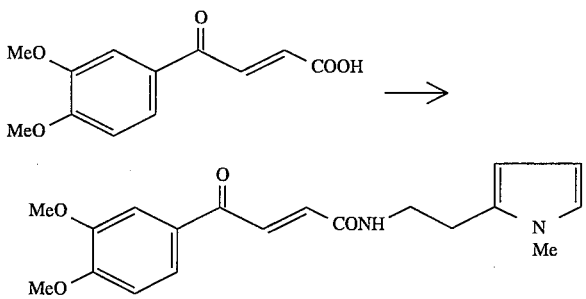

The above carboxylic acid amide was obtained in a manner similar to that in the preceding example. (Yield=57%)
mp 132°~134° C.

NMR(COCl₃. 250 MHz) δppm; 2.87 (2H, q, J=6.8 Hz) 3.62 (3H, S) 3.65 (2H, q, J=6.8 Hz) 3.95 (3H, S) 3.97 (3H, S) 5.94~5.96 (1H, m) 6.06~6.09 (1H, m) 6.10~6.20 (1H, m) 6.59 (1H, t J=2.5 Hz) 6.90 (1H, d, J=15 Hz) 6.93 (1H, d, J=8.5 Hz) 7.58(1H, d, J=2.0 Hz) 7.71 (1H, dd, J=8.5, 2.0 Hz) 7.99 (1H, d, J=15 Hz)

IR (KBr) cm⁻¹ 3379, 3009, 2970, 2937, 2843, 1672, 1643, 1591, 1577, 1545, 1514, 1446, 1415, 1298, 1267, 1228, 1159, 1143, 1018, 970, 906, 891, 814, 761, 709, 686, 623, 605

EXAMPLE 27

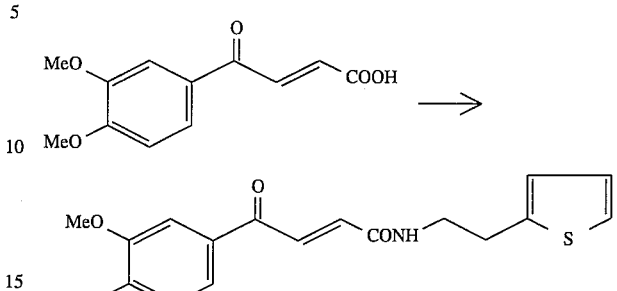

The above carboxylic acid amide was obtained in a manner similar to that in the preceding example. (Yield=59% )

NMR (COCl₃, 250 MHz) δppm; 3.95 (3H, S) 3.98 (3H, S) 4.77 (2H, d, J=5.7 Hz) 6.23~6.36 (1H, m) 6.93 (1H, d, J=8.4 Hz) 6.957 (1H, d, J=19.8 Hz) 6.959 (1H, dd, J=5.0, 1.5 Hz) 7.01~7.04 (1H, m) 7.25 (1H, dd, J=5.0, 1.3 Hz) 7.57 (1H, d, J=1.9 Hz) 7.71 (1H, dd, J=8.4, 1.9 Hz) 8.42 (1H, dd, J=14.8 Hz) m.p. 157°~159° C.

IR (KBr) cm⁻¹; 3323, 3055, 2937, 1676, 1643, 1591, 1572, 1518, 1464, 1444, 1346, 1317, 1275, 1221, 1192, 1172, 1132, 1020, 974, 852, 765, 733, 696, 621, 603.

The compounds of the invention were evaluated their tyrosine kinase inhibitory activities with partially purified EGF (epidermal cell growth factor) receptor preparation and cell growth inhibitory activity with human cancer cells.

Tyrosine Kinase Inhibitory Activity

Tyrosine kinase inhibitory activities of the compounds of the invention were determined as the inhibitory activities of the compounds added into the tyrosine kinase activity assay system.

Tyrosine kinase activity was measured using partially purified EGF receptor prepared from A431 cell line derived from human epidermoid carcinoma according to the method of Linda J. Pike et al (Proceedings of the National Academy of Sciences of the U.S.A., 79 1443, 1982).

The method employed is detailed below.

A431 cells were cultured in Dulbecco's modified Eagles medium (DMEM) containing 10% fetal calf serum (FCS) at 37° C. under 5% $CO_2$ atmosphere. The cultured cells were homogenated in a solution containing 10 mM N-2-hydroxy-ethylpiperazino-N'-2-ethane sulfonate buffer (pH 7.4), 0.25M sucrose, and 0.1 mM EDTA, and centrifuged at 3000 xg for 5 minutes. The supernatant was then centrifuged at 10000 xg for 30 minutes to obtain A431 cell membrane fraction. The cell membrane fraction, a partially purified EGF receptor, was used as an enzyme source. A test compound dissolved in dimethylsulfoxide (DMSO) was added to a reaction mixture containing 15 mM Hepes buffer (pH 7.7), 2 mM $MnCl_2$, 10 μM $ZnSO_4$, 50 μM $Na_3VO_4$ and the partially purified EGF receptor preparation (10–15 μg). To this mixture 100 ng EGF, 75 μg synthetic substrate RR-SRC peptide (Arg-Arg-Leu-Ile-Glu-Asp-Ala-Glu-Tyr-Ala-Ala-Arg-Gly) and 10 μM γ-³²P-adenosine triphosphate (55.5 KBq) were added thereto to start the reaction. The mixture was allowed to react under ice-cooling-O for 30 minutes, and the reaction was stopped by addition of 10 mg/ml bovine serum albumin and 20% trichloroacetic acid. The reaction mixture was left to stand under ice-cooling for 30 minutes. The mixture was centrifuged at 5000 xg for two minutes, and an aliquot of the supernatant was adsorbed on P81 phosphocellulose filter. The filter was dipped in 30% aqueous acetic acid for 15 minutes for fixation and then washed with 15% acetic acid. The washing was repeated four times. The radioactivity of $^{32}P$ retained on the phosphocellulose filter was counted with liquid scintillation counter.

Tyrosine kinase inhibitory activity (TKIA) was determined according to the following equation:

$$TKIA(\%)=\{1-(B-C)/(A-C)\}\times 100$$

The sympols "A", "B" and "C" represent the radioactivities determined in tyrosine kinase assays with test compounds, without a test compound, and without both a test compound and EGF, respectively. The value $IC_{50}$ (concentration of a test compound providing 50% inhibition) was calculated from TKIA values at various concentrations of a test compound in the above-described test procedure.

Cancer Cell Growth Inhibitory Activity

KB cell, which is a human rhinopharyngeal cancer cell, possesses overexpression of EGF receptors. Accordingly, the KB cell was used to evaluate the effect of test compounds on the growth of cultured cancer cells.

KB cells were plated on a 96-well dish ($2.5\times 10^3$ cell/well) and cultured for 24 hours at 37° C. under 5% $CO_2$ atmosphere in DMEM:F12 (1:1) medium containing 10% FCS, 50 μg/ml penicillin, and 50 μg/ml streptomycin. To the culture medium was added a test compound dissolved in DMSO (DMSO final concentration<0.1%), and the cells were cultured for three days under the same conditions. The test compound was exchanged every 24 hours together with the culture medium.

The amount of living cells were measured by calorimetric determination at wave lengths of 550 nm and 650 nm after developing colour by MTT reagent, in accordance with the method of Michael C. Alley (Cancer Research 48 589, 1988).

Cancer cell growth inhibitory activity (CCGIA) was determined according to the following equation.

$$CCGIA(\%)=(b-a)/b\times 100$$

Simbols "a" and "b" represent the colorimetric values determined in the cancer cell growth assay with and without the test compounds, respectively. The value $IC_{50}$ (concentration of a test compound providing 50% inhibition) was calculated from CCGIA values at various concentration of a test compound in the above-described procedure.

Results are shown in Table 2, wherein "Compound No" in the first column corresponds to that in Table 2.

TABLE 2

| compound | Inhibitory activity ($IC_{50}$, μM) | |
|---|---|---|
| No. | Tyrosine kinase | Cancer cell growth |
| 2 | 0.32 | 0.92 |
| 19 | 0.79 | 0.97 |
| 45 | 1.0 | 0.22 |
| 58 | 2.2 | 0.34 |
| 59 | 0.54 | 0.45 |
| 60 | 1.0 | 1.85 |
| 61 | 1.5 | 2.0 |
| 64 | 1.5 | 1.1 |
| 67 | 13.0 | 0.58 |
| 71 | 1.2 | 1.2 |

TABLE 2-continued

| compound | Inhibitory activity ($IC_{50}$, μM) | |
|---|---|---|
| No. | Tyrosine kinase | Cancer cell growth |
| 74 | 0.76 | 0.7 |
| 75 | 4.3 | 1.25 |
| 83 | 0.81 | 0.95 |
| 110 | 0.91 | 11.5 |

As shown in Table 2, the benzoylacrylamide derivatives of the present invention possess potent inhibitory-activities on tyrosine kinase and cancer cell growth, and therefore, they are useful as anti-cancer agents.

What is claimed is:

1. A pharmaceutical composition which comprises a pharmaceutically effective amount of a compound of the formula

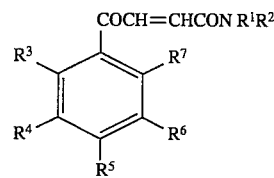

wherein $R^1$ represents a hydrogen atom, $R^2$ represents $-(CH_2)_m-A$ wherein m is an integer of 0 to 3, and A represents pyridyl which is unsubstituted or is substituted by $C_1-C_3$ alkyl said alkyl being unsubstituted or substituted by phenyl, and $R^3$, $R^4$, $R^5$, $R^6$ and $R^7$ each independently represent a hydrogen atom, a halogen atom, $C_1-C_5$ alkyl which is unsubstituted or is substituted with a halogen atom or $-OR^{13}$ wherein $R^{13}$ represents a hydrogen atom or $C_1-C_5$ alkyl which is unsubstituted or is substituted with a halogen atom or phenyl, or when their adjacent substituents are taken together, they represent $C_1-C_3$ oxyalkylene having one or two oxygen atoms;

or a pharmaceutically acceptable salt thereof, and a pharmaceutically acceptable carrier therefor.

2. A method for suppressing the growth of cancer cells in mammals which comprises administering to a mammal in need of such treatment an effective amount of a compound of the formula

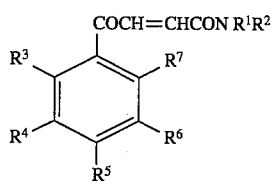

wherein $R^1$ represents a hydrogen atom, $R^2$ represents $-(CH_2)_m-A$ wherein m is an integer of 0 to 3, and A represents pyridyl which is unsubstituted or is substituted by $C_1-C_3$ alkyl said alkyl being unsubstituted or substituted by phenyl, and $R^3$, $R^4$, $R^5$, $R^6$ and $R^7$ each independently represent a hydrogen atom, a halogen atom, $C_1-C_5$ alkyl which is unsubstituted or is substituted with a halogen atom or $-OR^{13}$ wherein $R^{13}$ represents a hydrogen atom or $C_1-C_5$ alkyl which is unsubstituted or is substituted with a halogen atom or phenyl, or when their adjacent substituents are taken together, they represent $C_1$–$C_3$ oxyalkylene having one or two oxygen atoms;

or a pharmaceutically acceptable salt thereof.

3. A benzoylacrylamide derivative represented by the formula:

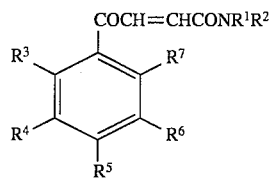

wherein $R^1$ represents a hydrogen atom, $R^2$ represents —$(CH_2)_m$-A wherein m is an integer of 0–3 and A is a pyridyl which is unsubstituted or is substituted by $C_1$–$C_3$ alkyl said alkyl being unsubstituted or substituted by phenyl, and $R^3$, $R^4$, $R^5$, $R^6$ and $R^7$ each independently represents a hydrogen atom or —$OR^{13}$ wherein $R^{13}$ represents a hydrogen atom or $C_1$–$C_5$ alkyl which is unsubstituted or is substituted by a halogen atom or phenyl, or a pharmaceutically acceptable salt thereof.

4. A compound of claim 3 wherein A is pyridyl.

5. A compound of claim 3 or claim 4 wherein $R^3$, $R^6$ and $R^7$ are hydrogen and $R^4$ and $R^5$ are each independently —$OR^{13}$ wherein $R^{13}$ is $C_1$–$C_3$ alkyl.

* * * * *